United States Patent [19]

Kunst et al.

[11] Patent Number: 5,342,788
[45] Date of Patent: Aug. 30, 1994

[54] METHOD AND STANDARD SOLUTION FOR THE DETERMINATION OF THYROXINE ($T_4$) OR TRIIODOTHYRONINE ($T_3$)

[75] Inventors: Albert Kunst, Pfungstadt; Helmut Rehner, Weilheim; Peter Stegmüller, Augsburg; Helmut Lenz, Tutzing; Peter Bialk, Eberfing; Nicholas Hoyle, Tutzing, all of Fed. Rep. of Germany

[73] Assignee: Boehringer Mannheim GmbH, Mannheim-Waldhof, Fed. Rep. of Germany

[21] Appl. No.: 998,463

[22] Filed: Dec. 29, 1992

Related U.S. Application Data

[63] Continuation-in-part of Ser. No. 337,353, Apr. 13, 1989, abandoned.

[30] Foreign Application Priority Data

Apr. 15, 1988 [DE] Fed. Rep. of Germany ....... 3812609
Aug. 14, 1992 [DE] Fed. Rep. of Germany ....... 4226949

[51] Int. Cl.$^5$ .................. G01N 33/78; G01N 33/96
[52] U.S. Cl. ..................... 436/500; 436/16; 436/18; 435/967
[58] Field of Search ............ 436/500, 16; 435/967

[56] References Cited

U.S. PATENT DOCUMENTS

| | | | |
|---|---|---|---|
| 4,052,504 | 10/1977 | Hertl et al. | 436/500 |
| 4,157,895 | 6/1979 | Finlay et al. | 436/500 |
| 4,381,291 | 4/1983 | Ekins | 436/500 |
| 4,431,741 | 2/1984 | Lewis et al. | 436/500 |
| 4,966,838 | 10/1990 | Ferrua et al. | 436/500 |
| 5,196,349 | 3/1993 | Piran et al. | 436/500 |

FOREIGN PATENT DOCUMENTS

| | | | |
|---|---|---|---|
| 337466 | 10/1989 | European Pat. Off. | 436/500 |
| 337467 | 10/1989 | European Pat. Off. | 436/500 |

OTHER PUBLICATIONS

Antibodies Incorporated Kit insert, Jan. 1976, pp. 1–8.
Ilyes et al., Chem. Abst. 92(19): 160009n (1980).
Schroeder et al., Clin. Chem. 32(5): 826–830 (1986).
Ito et al., Clin. Chem. 30(10): 1682–1685 (1984).

*Primary Examiner*—Christine M. Nucker
*Assistant Examiner*—Chris Dubrule
*Attorney, Agent, or Firm*—Felfe & Lynch

[57] ABSTRACT

A standard solution containing thyroxine-binding globulin (TBG) and thyroxine or triiodothyronine dissolved in a buffer solution is used for calibration in a method for the determination of thyroxine ($T_4$) or triiodothyronine ($T_3$) in serum, wherein both human and bovine TBG can be used.

13 Claims, 4 Drawing Sheets

METHOD AND STANDARD SOLUTION FOR THE DETERMINATION OF THYROXINE (T4) OR TRIIODOTHYRONINE (T3)

RELATED APPLICATIONS

This application is a continuation-in-part application of copending application Ser. No. 337,353 which was filed on Apr. 13, 1989.

FIELD OF THE INVENTION

The invention concerns a method for the determination of thyroxine ($T_4$) or triiodothyronine ($T_3$) in serum using a standard solution as well as this standard solution.

BACKGROUND OF THE INVENTION

The thyroid hormones are present in blood mainly in a protein-bound form. The most important carrier protein for this is thyroxine-binding globulin, which is denoted TBG, to which ca. 80% of the total thyroxine and triiodothyronine present in blood is bound. Approximately 5 to 10% of the total thyroxine present is bound to albumin and about 10 to 15% of the total thyroxine present is bound to pre-albumin. The totality of these proteins is also referred to as thyroxine-binding protein (TBP). Only very small proportions of thyroxine and triiodothyronine is present in blood in a free form; usually ca. 0.03% of $T_4$ or 0.3% of $T_3$. Only the released hormones are physiologically active whereas the bound hormones $T_3$ and $T_4$ circulate in the blood as a metabolically inert transport form and serve as a buffer to regulate the level. It is therefore important to determine the total thyroxine content as well as the proportion of free thyroxine and free triiodothyronine in blood since this represents the functional thyroid status independent of changes in the concentration or saturation of the thyroxine binding protein.

Various methods are known for the determination of total thyroxine ($T_4$), free thyroxine ($FT_4$) and triiodothyronine ($T_3$). A difficulty in all of these known methods is the provision of a standard which is suitable for the calibration.

For the calibration it is necessary to produce human serum standards with particular thyroxine or triiodothyronine concentrations and a defined $FT_4$ or $FT_3$ content. Human serum has previously been used as starting material for this. Firstly all the thyroxine and triiodothyronine in a free as well as in a bound form must be removed from the human serum and then the human serum treated in this way is supplemented with known levels of thyroxine or triiodothyronine. Various methods are described in the literature for this purpose such as treatment with active charcoal, with ion exchangers or with carrier-bound anti-$T_4$ or anti-$T_3$ antibodies. These methods are all very complicated. A further problem is that each human serum sample has a different composition thus leading to large variations in the individual lots and as a consequence the reproducibility leaves much to be desired.

A further disadvantage of these known standard solutions for the determination of $T_3$ and $T_4$ is that these solutions, containing human serum, cannot be stored for longer periods since, on the one hand, the protein which is present is gradually denatured and on the other hand there is a shift in the set equilibrium between bound and free $T_3$ and $T_4$.

It is known from EP-A 0 337 467 that in order to solve the above-mentioned problems, a standard solution can be used to determine thyroxine or triiodothyronine levels which is still stable after long periods of time and can be produced in a simple manner using relatively cheap starting materials by using at least one standard solution for the calibration that contains TBG and thyroxine or triiodothyronine dissolved in a buffer solution.

It was established that, in a solution containing TBG and thyroxine or triiodothyronine dissolved in a buffer system, the equilibrium which establishes between bound and free $T_4$ or $T_3$ is just as in human serum. Surprisingly, the incomplete equilibration system according to the present invention, in which components of the natural thyroxine-binding proteins are missing, yields even better comparative values than a natural matrix based on human serum which was first made free from and then augmented with thyroid hormone, so that after appropriate calibration such solutions can be used as standard solutions. Thus, in accordance with the present invention a standard solution is provided for a process to determine thyroxine or triiodothyronine which is simple to produce.

Accordingly, it was an object of the present invention to provide a standard solution for a process to determine thyroxine or triiodothyronine which is also stable after longer storage and which can be produced in a simple manner using cheap raw materials.

This object was achieved by a process for the determination of thyroxine or triiodothyronine in serum wherein at least one standard solution is used for calibration containing TBG and thyroxine or triiodothyronine respectively dissolved in a buffer solution.

It has also been found that a further quite considerable improvement of the stability on storage can be achieved if TBG from bovine serum is used in the aforementioned methods.

SUMMARY OF THE INVENTION

The invention therefore concerns a method for the determination of thyroxine ($T_4$) or triiodothyronine ($T_3$) in serum in which a standard solution is used for the calibration which contains thyroxine-binding globulin (TBG) and thyroxine or triiodothyronine dissolved in a buffer solution.

It is a further embodiment of the invention to use a bovine serum which allows for considerable improvement in the stability of the standard solutions.

DETAILED DESCRIPTION OF THE INVENTION

Figure 1:
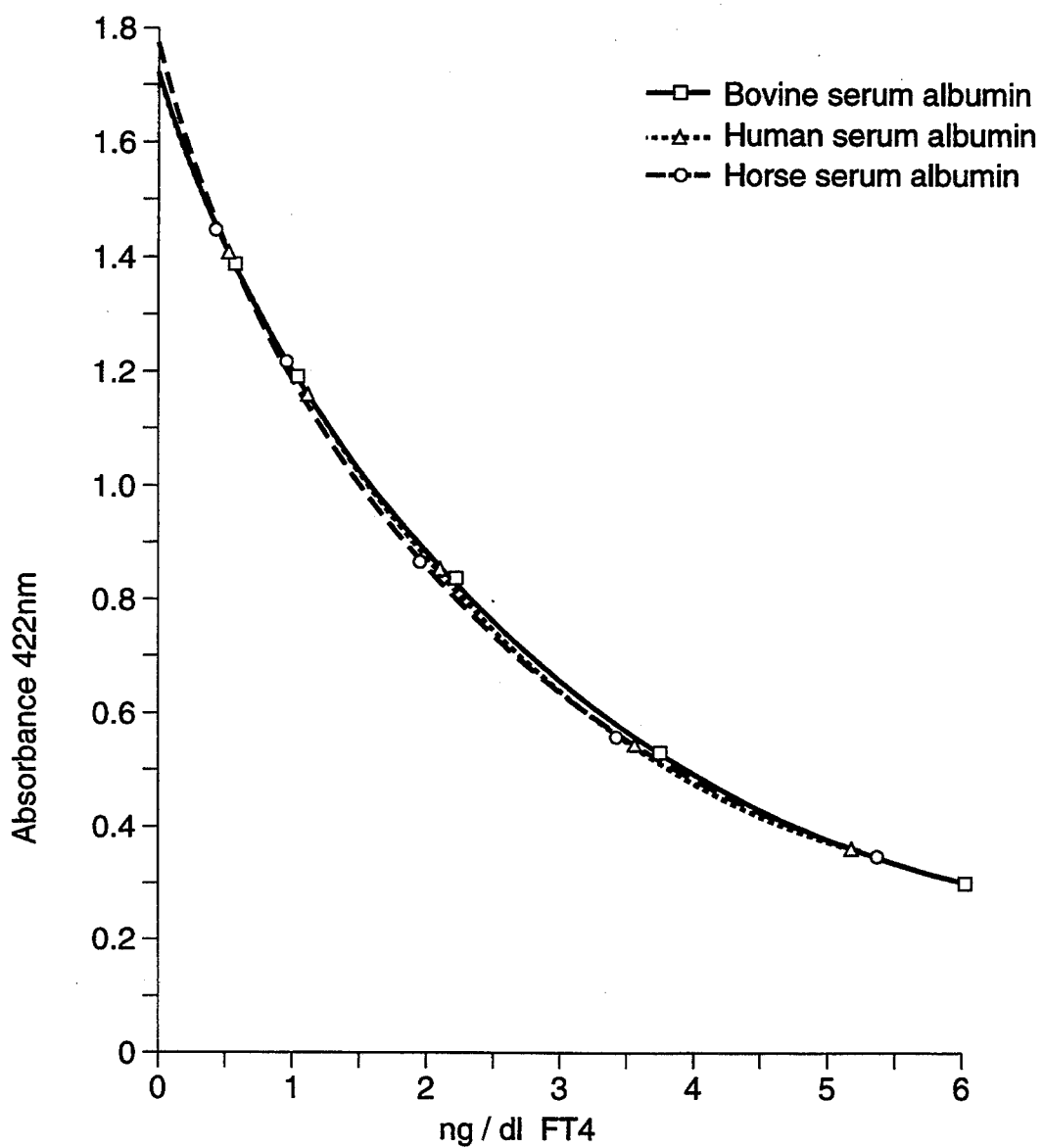
FIG. 1 shows a calibration curve for different thyroxine concentrations which were obtained by determining $FT_4$ using a heterogeneous immunoassay.

Various methods are known for determining thyroxine and triiodothyronine. Methods of determination are for example described in Nuc. Compact 16 (1985), 321–327, J. Clin. Immunoassay 7 (1984), 192–205, and J. Clin. Chem. Clin. Biochem. 22 (1984), 895–904. Determination methods based on immunoassays are especially useful for determining thyroid hormones.

In a known method for the determination of thyroxine or triiodothyronine in serum based on an immunoassay technique, labelled $T_4$ or $T_3$ and $T_4$ or $T_3$ from the sample compete for a binding partner such as an anti-$T_4$ antibody. By adjusting the reaction conditions such as the concentration of the individual components, incubation period etc., it is possible to determine either the total thyroxine, total triiodothyronine, thyroxine or triiodothyronine content in the presence of thyroxine or triiodothyronine bound to TBG or the free thyroxine or free triiodothyronine. For this, the amount of labelled $T_3$ or $T_4$ bound to the anti-$T_4$ or anti-$T_3$ antibody or non-bound, labelled $T_3$ or $T_4$ is determined via known detection reactions. After measuring the label, the content of $T_3$ or $T_4$ can then be calculated by comparing the value obtained to values obtained with known $T_3$ or $T_4$ concentrations. For this it is necessary to establish a calibration curve in which the measurement signal (e.g. the absorbance value) is plotted against the $T_3$ or $T_4$ concentration. In the case of thyroxine, it is desirable to establish a calibration curve from six thyroxine solutions with different concentrations since there is no linear relationship which would allow a two-point standard measurement.

The thyroxine-binding globulin ("TBG") can be isolated from sera in a known manner. The standard solution used according to the present invention preferably contains 5 to 30 µg/ml TBG. It is particularly preferred to use TBG in a physiological amount which is in the range from 9 to 20 µg/ml TBG which, for example can be gathered from Lab. Med. 6 (1982), 27–29, and J. Clin. Chem. Clin. Biochem 23 (1985) 117–127 the subject matter of which is incorporated herein by reference.

If the standard solution is to be used to determine thyroxine, it contains thyroxine. The thyroxine is preferably present in an amount of ranging from 5 to 500 ng/ml. It is particularly preferable to add a physiological amount of thyroxine to the standard solution i.e. an amount in a range of from 5 to 300 ng/ml.

If the standard solution is to be used to determine triiodothyronine, it contains triiodothyronine. The triiodothyronine is preferably used in an amount in the range of from 0.5 to 12 ng/ml. It is particularly preferable to add triiodothyronine in a physiological amount, i.e. in the range of from 0.5 to 8 ng/ml.

The standard solution used for the method according to the present invention preferably also contains albumin, which improves the stability of the standard solutions containing TBG alone and solutions also containing thyroxine or triiodothyronine in buffer solution. In this connection, it is not necessary to add human serum albumin, which is of course suitable, to the standard solution preferred according to the present invention. Equally suitable are the universally and easily obtainable and much more preferable albumins, for example from bovine or horse serum. Human serum albumin, bovine serum albumin or horse serum albumin and particularly bovine serum albumin, is preferably used as the albumin. The albumin is preferably used in an amount of 40 to 80 mg/ml. It is particularly preferable to use albumin in a physiological amount, i.e., at a range of from 50 to 70 mg/ml.

In order to produce the standard solution, TBG and, if desired, albumin are dissolved in a buffer solution. All buffers which have a pH range of 6.0 to 8.0 are suitable as the buffer system, preferably those with a pH value of 6.5 to 7.5. GOOD buffers are preferably used, for example HEPES or TRIS buffer. The buffer concentration is not critical, however the buffer is preferably used at a concentration of 30 to 150 mmol/l. The standard solution particularly preferably contains 50 to 100 mmol/l buffer.

Subsequently the thyroxine and/or triiodothyronine in appropriate concentrations is added to this solution. In this process an equilibrium is established between bound protein and free thyroid hormones, which is similar to the equilibrium which is present in vivo in blood. This solution is also stable over long periods of storage because of its composition. Since it is produced from standardized individual substances, it always has a uniform composition and therefore yields reproducible values.

In order to establish a calibration curve, several standard solutions—as a rule four to six—are used with different contents of thyroid hormones so that a curve can be drawn from the values obtained. In a preferred embodiment of the method according to the present invention, the first standard solution contains TBG and, if desired, albumin in a buffer solution but contains no thyroid hormone. Solutions with known hormone contents are then used for further calibration.

Standard solutions in liquid reagent form ordinarily can only achieve a storage capability of eight weeks and are therefore typically stored in a lyophilized form. The standard solution utilizing TBG isolated from human sera allows for stability in liquid form for at least eight weeks.

Standard solutions for the determination of thyroxine or triiodothyronine which contain bovine TBG. and thyroxine or triiodothyronine dissolved in a buffer system are also useful according to this invention.

Solutions which incorporate bovine TBG isolated from bovine serum surprisingly allow for improved storage stability. In fact, increased stability is present for more than 10 times longer than using TBG isolated from human sera sample.

According to the results obtained thus far, the standard solutions containing bovine TBG in liquid form remain stable for at least 18 months. After this time period, there is still a full binding capacity for $T_4$ and $T_3$. In comparison, the corresponding standard solution with human TBG, even when stored below 10° C., yields erroneous values which are 20% higher after a twelve week storage period. Moreover the bovine serum used to isolate bovine TBG is much more readily obtainable than human serum.

The standard solution preferably contains in a range from 5 to 30 µg/ml bovine TBG. It is particularly preferred that a physiological amount of bovine TBG, i.e. 9 to 20 µg/ml, is present in the standard solution.

According to the invention a standard solution with a superior stability is provided which can be produced in a simple manner from easily obtainable starting materials.

This invention will be better understood by reference to the following examples, which are included here for purposes of exemplification and are not to be considered as limitative.

EXAMPLE 1

Solutions containing different thyroxine concentrations were prepared. The solutions had the following composition:
50 mmol/l HEPES-buffer pH 7.0;
60 mg/ml bovine serum albumin;
15 μg/ml human thyroxine-binding globulin (TBG).
Increasing quantities of $T_4$ were added to this solution to yield the following concentrations of free thyroxine after equilibrium was established: 0; 0.9; 1.5; 2.5; 4.3; 6.5 ng $FT_4$/dl.

In addition, solutions with the same compositions were prepared which, however, contained human serum albumin or horse serum albumin instead of bovine serum albumin.

The following reagents were used to determine the free thyroxine:
Reagent 1: 55 mmol/l barbital buffer, pH 7.8; 10 mU/ml $T_4$-peroxidase-conjugate;
Reagent 2: 1.9 mmol/l ABTS (2,2′-azino-di-[3-ethyl-benzthiazoline-6-sulphonate]-diammonium salt); 3.2 mmol/l sodium perborate; 100 mmol/l phosphate/citrate buffer, pH 4.4.

As reaction vessels, polystyrol tubes were used which were coated with polyclonal anti-$T_4$-antibodies.

1 ml of Reagent 1 and 20 μl of the standard solution were pipetted into these tubes and incubated for 60 minutes at room temperature. The tubes were then aspirated and washed with tap water. Afterwards 1 ml of Reagent 2 was added and incubated for 30 minutes at room temperature. The absorbance was then measured photometrically at 405 nm or 422 nm.

The absorbance readings corresponding to each of the standard concentrations were plotted on graph paper and a curve was then drawn which is shown in FIG. 1. From the absorbances of the measured samples, the $FT_4$ concentrations can be read from the calibration curve. It can be seen that bovine and horse serum albumin yield the same values as human serum albumin.

EXAMPLE 2

A standard solution was prepared according to the present invention and stored over a long period under the conditions indicated. Parallel to this, standard solutions were prepared according to conventional methods of the prior art, i.e., solutions of increasing quantities of thyroxine in $T_4$-free human serum, and stored in an analogous fashion. The long and short term stability of the standard solutions were then examined.

The solutions prepared according to Example 1 were used as standard solutions according to the present invention and contained respectively 0; 0.9; 1.5; 2.5; 4.3; and 6.5 ng $FT_4$/dl.

Following preparation, these solutions were lyophilized and stored for three weeks at 35° C. After reconstitution they were stored for a further eight weeks in solution at 4° C. The solutions were then employed for a determination of $FT_4$ as described in Example 1.

The average recovery of the standard absorbances before and after storage is shown in the following Table I:

TABLE I

| Standard | Before storage | After |
| --- | --- | --- |
| standard solution according to the present invention | 100% | 99% |
| human serum standard | 100% | 89% |

As can be seen from these values the standard solution according to the present invention is very much more stable than human serum solutions of the prior art.

EXAMPLE 3

The recovery of $FT_4$ was examined in 21 human sera sample. The determination of $FT_4$ was carried out at 20° C. or 30° C. as described in Example 1. The same standard solutions were used as in Example 2. These solutions were lyophilized and stored for three weeks at 35° C. Afterwards the lyophilizates were reconstituted and stored for a further two weeks in solution at 25° C.

As the results of Table II show, recovery is independent of temperature when calibration is performed with the standard solution according to the present invention even after long periods of storage. In contrast, using the more unstable human serum standard solutions, different $FT_4$ concentrations were measured at 20° C. and 30° C.

TABLE II

| Standard | Average recovery of 21 human sera at 30° C. in comparison to recovery at 20° C. |
| --- | --- |
| Standard solution according to the present invention | −0.3% |
| human serum standard solution | −19.0% |

EXAMPLE 4

Standard solutions prepared according to Example 1 were used for a $T_4$ test.

The following reagents were used for this:
Reagent 1: 120 mmol/l barbiturate; 18.2 mmol/l phosphate-buffer, pH 8.6; 1.27 mmol/l ANS (8-anilino-1-naphthalenesulfonic acid);
15 Mu/ml $T_4$-peroxidase-conjugate;
Reagent 2: composition as described in Example 1.

As reaction vessels, polystyrol tubes were used which were coated with polyclonal anti-$T_4$-antibodies.

1 ml of Regent 1 and 20 μl of the standard solution were pipetted into these tubes and incubated for 30 minutes at room temperature. The tubes were then aspirated and washed with tap water. Afterwards 1 ml of Reagent 2 was added and incubated for 30 minutes at room temperature. The absorbance was then measured photometrically at 405 nm or 422 nm.

Figure 2:
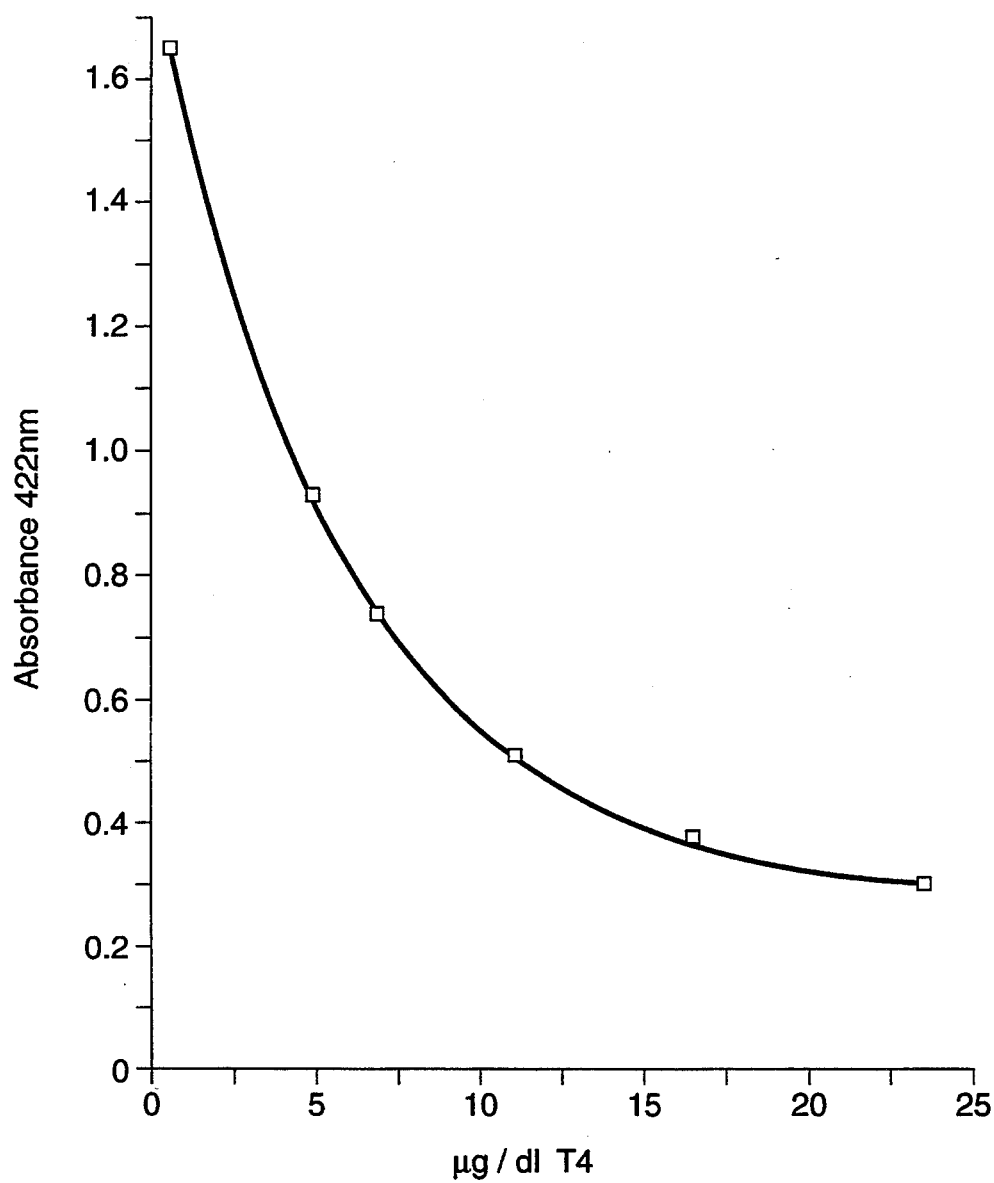
FIG. 2 shows a calibration curve for different $T_4$ concentrations which were used for the determination of total thyroxine.

The absorbance readings corresponding to each of the standard concentrations were plotted on graph paper and a curve was then drawn which is shown in FIG. 2.

EXAMPLE 5

Solutions containing different triiodothyronine concentrations were prepared. The solutions had the following composition:
50 mmol/l HEPES-buffer, pH 7.0;
60 mg/ml bovine serum albumin;

15 μg/ml human thyroxine-binding globulin (TBG). Increasing quantities of $T_3$ were added. Standard solutions prepared in this way were employed in a $T_3$-test. For this the following reagents were used (concentrations of the ready-to-use solutions):

Reagent 1: 120 mmol/l barbiturate; 18.2 mmol/l phosphate-buffer, pH 8.6; 1.27 mmol/l ANS (8-anilino-1-naphthalene-sulfonic acid); 12 mU/ml $T_3$-peroxidase-conjugate.

Reagent 2: 100 mmol/l phosphate-citrate-buffer, pH 5.0; 1.47 mmol/l sodium perborate; 9.1 mmol/l ABTS (2,2'-azino-di-[3-ethyl-benzthiazoline-6-sulphonate]-diammonium salt).

As reaction vessels, polystyrol tubes were used which were coated with polyclonal anti-$T_3$-antibodies.

Figure 3:
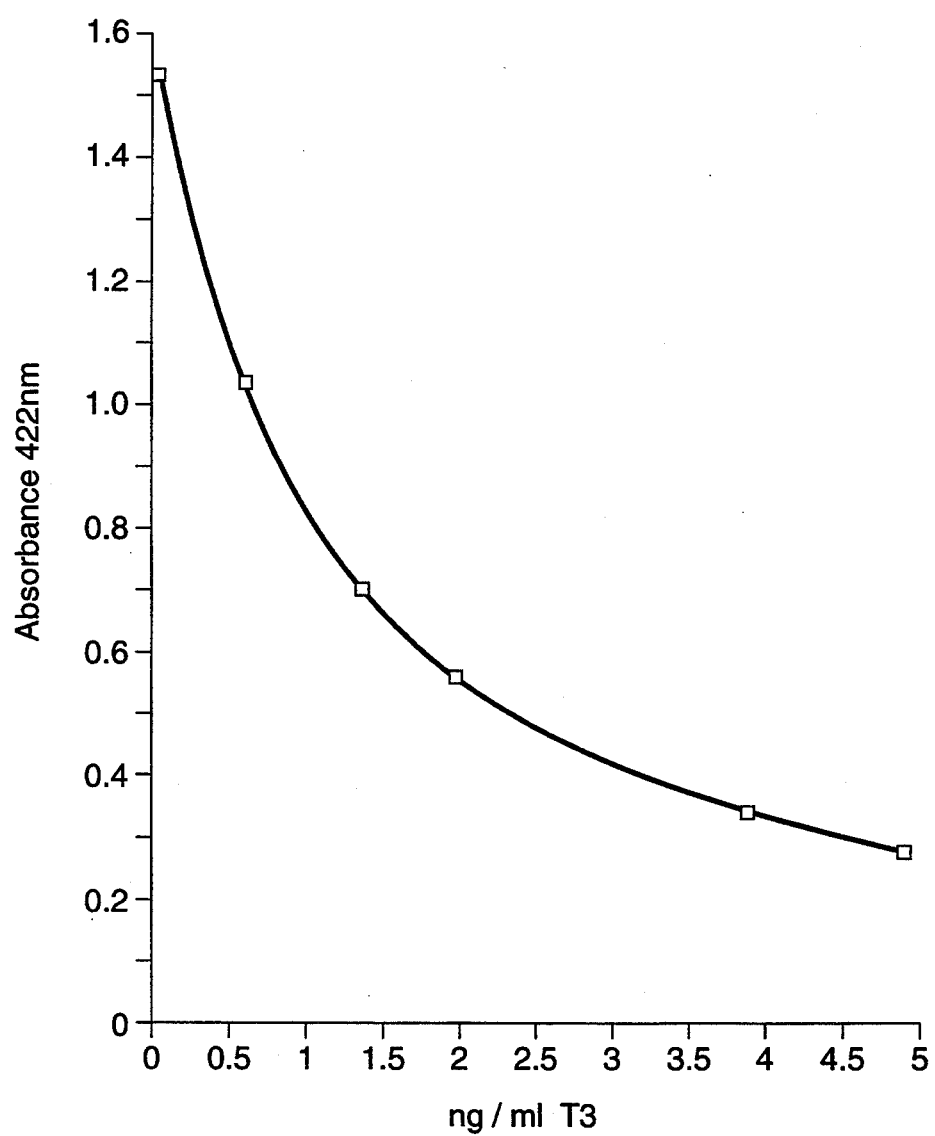
FIG. 3 shows a calibration curve for different $T_3$ concentrations which can be used for the determination of total triiodothyronine.

1 ml of Reagent 1 and 100 μl of the standard solution were pipetted into these tubes and incubated for 2 hours at room temperature. The tubes were then aspirated and washed with tap water. Afterwards 1 ml of Reagent 2 was added and incubated for 60 minutes at room temperature. The absorbance was then measured photometrically at 405 nm or 422 nm. The results are shown in FIG. 3.

EXAMPLE 6

Isolation of Bovine TBG

Bovine plasma is brought to a concentration of 2 mol/l ammonium sulfate. The supernatant is decanted off, diluted to 1 mol/l ammonium sulfate and applied to a chromatography column (Sepharose, to which $T_4$ is bound). It is washed in succession with:

1. 50 mmol/l Tris pH 7.5, 100 mmol/l sodium chloride
2. 50 mmol/l Tris pH 7.5, 750 mmol/l sodium chloride
3. 50 mmol/l Tris pH 7.5, 100 mmol/l sodium chloride
4. 50 mmol/l Tris pH 7.5, 100 mmol/l sodium chloride 5 mmol/l 8-anilino-naphthalene sulfonic acid.

The eluate is concentrated in an osmotic cell and 8-anilinonaphthalene sulfonic acid is removed by dialyzing for two days against 5 mmol/l sodium phosphate pH 7.5, 10 mmol/l sodium chloride.

EXAMPLE 7

Stability of $T_3/T_4$ calibrators
Composition of the calibrators:
6% bovine serum albumin,
50 mmol/l HEPES buffer, pH 7.4
15 μg/ml bovine TBG
$FT_3$ content: 0, 2, 7, 15, 30 pg/ml
or $FT_4$ content: 1, 10, 20, 40, 80 pg/ml
The following Table III shows the stability of $T_3/T_4$ calibrators.

|  | Storage period at 4-8° C. (months) | Recovery[1] with an analyte content of 2-30 pg/ml |
|---|---|---|
| $T_3$ without TBG | 3 | 118 |
|  | 6 | 130 |
|  | 12 | — |
| $T_3$ with human TBG | 3 | 115 |
|  | 6 | 130 |
|  | 12 | 138 |
| $T_3$ with bovine TBG | 3 | 100 |
|  | 6 | 97 |
|  | 12 | 99 |

[1]The recovery shows the measurement value found for $T_3$ in relation to the measurement value for $T_3$ at the beginning of storage (100%).

Figure 4:
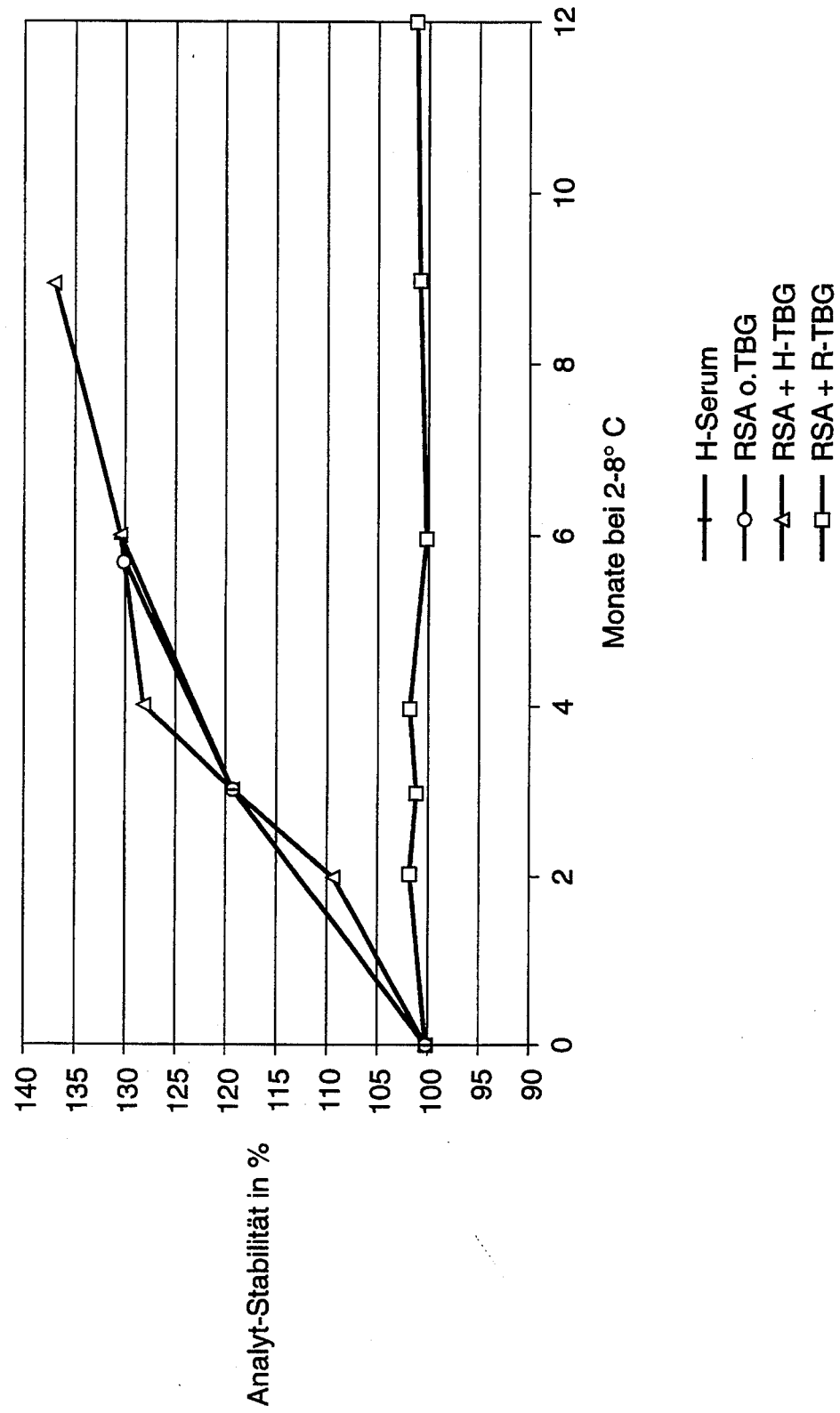
FIG. 4 shows stability of analyte solutions utilizing H-serum, RSA without TBG, RSA and H-TBG and RSA and R-TBG measured at 2°–80° C. for a 12 month period.

The increased stability of the standard solution with use of bovine isolated TBG can be seen in FIG. 4. From this it is apparent that with human TBG (H-TBG), the analyte stability decreases rapidly so that erroneously high values are found which are already 20% higher after three months, i.e., 120% of the initial value, than with a fresh solution. In contrast, using the standard solution according to the present invention, no change whatsoever can be observed even after 12 months: the analytical values are unchanged and correct at 100%. The stated contents in percent relate to the measured recovery of analyte compared to a fresh product. Here it should be noted that analyte bound to TBG, i.e. $T_4$ or $T_3$, is not detected at all and an increase in the value for $T_4$ or $T_3$ means that the binding to TBG has deteriorated thus yielding false values compared to fresh natural TBG. The limit which is still just acceptable is a change of ±5%.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for determining the total amount of a substance selected from the group consisting of thyroxine (T4) and triiodothyronine (T3) in serum comprising assaying a serum sample and calibrating said assay by assaying a first serum-free standard solution under conditions identical to conditions employed in assaying said serum sample, wherein said first serum-free standard solution contains a known amount of bovine thyroxine-binding globulin (TBG), a known amount of albumin and a known amount of a substance selected from the group consisting of thyroxine and triiodothyronine, and a buffer, and assaying at least a second additional serum-free standard solution under said identical conditions which contains the same amount of bovine thyroxine-binding globulin as said first serum-free standard solution, a known amount of albumin and neither thyroxine or triiodothyronine in a buffer containing solution.

2. Method of claim 1, wherein said first standard solution and said second additional standard solution contain a known amount of albumin.

3. Method of claim 2, wherein said albumin is bovine serum albumin.

4. Method of claim 2, wherein said albumin is present in an amount from 40-80 mg/ml.

5. Method of claim 1, wherein said standard solution contains 5-30 μg TBG/ml of solution.

6. Method of claim 1, wherein said standard solution contains 9-20 μg TBG/ml of solution.

7. Method of claim 1, wherein said first standard solution contains from 5-500 ng/ml thyroxine.

8. Method of claim 1, wherein said first standard solution contains from 5-300 ng/ml thyroxine.

9. Method of claim 1, wherein said first standard solution contains from 0.5 to 12 ng/ml triiodothyronine.

10. Method of claim 1, wherein said first standard solution contains from 0.5 to 8 ng/ml triiodothyronine.

11. Method of claim 1, wherein said first standard solution is buffered at a pH of from 6 to 8.

12. Method of claim 1, wherein said buffer is a GOOD buffer.

13. Method of claim 1, wherein said buffer is present in an amount of from 30 to 150 mmol/liter.

* * * * *